United States Patent [19]

Pfirrmann

[11] Patent Number: 6,117,868

[45] Date of Patent: Sep. 12, 2000

[54] TREATMENT OF GASTROINTESTINAL ULCERS OR GASTRITIS CAUSED BY MICROBIAL INFECTION

[75] Inventor: Rolf W. Pfirrmann, Lucerne, Switzerland

[73] Assignee: Ed. Geistlich Sohne AG fur chemische Industrie, Switzerland

[21] Appl. No.: 09/316,115

[22] Filed: May 20, 1999

Related U.S. Application Data

[63] Continuation-in-part of application No. 09/154,451, Sep. 16, 1998, abandoned.

[51] Int. Cl.$^7$ .................................................. A61K 31/54
[52] U.S. Cl. .................. 514/222.5; 514/525; 514/926; 514/927
[58] Field of Search ................................ 514/222.5, 925, 514/926, 927

[56] References Cited

U.S. PATENT DOCUMENTS

| | | | |
|---|---|---|---|
| 3,423,408 | 1/1969 | Pfirrmann | 260/243 |
| 5,256,684 | 10/1993 | Marshall | 514/398 |
| 5,599,794 | 2/1997 | Eek et al. | 514/338 |

*Primary Examiner*—Frederick Krass
*Attorney, Agent, or Firm*—Rothwell, Figg, Ernst & Manbeck, P.C.

[57] ABSTRACT

A method and composition for the treatment of infectious gastrointestinal ulcer disease or infectious gastritis disease of microbially infected gastrointestinal tissue in a mammal involves administration of an antimicrobial amount of an antimicrobial medicament which is cell wall constituent-inactivating by chemical reaction with cell wall constituents, endotoxin non-releasing, exotoxin-inactivating or a combination thereof.

13 Claims, No Drawings

TREATMENT OF GASTROINTESTINAL ULCERS OR GASTRITIS CAUSED BY MICROBIAL INFECTION

CROSS-REFERENCE TO RELATED APPLICATIONS

The present application is a continuation-in-part of U.S. Ser. No. 09/154,451 filed Sep. 16 1998, now abondoned.

BACKGROUND OF THE INVENTION

1. Field of the Invention

The present invention relates to the field of treating patients having gastrointestinal ulcers or gastritis caused by microbial infection.

2. Description of the Background Art

The stomach's infection with the germ *Heliobacter pylori* (*H.p.*) is one of the most frequent infectious diseases in the world; in developing countries, more than 80% of the population is already infected with *H.p.* during childhood.

In the past, chronic gastritis with prolonged dyspeptic symptoms in the upper stomach, the peptic ulcer, duodenal ulcer (UD) and ventral ulcer (UV) with pain in the upper stomach after meals or epigastric pain on empty stomach being a syndrome with unclear etiology. Its pathogenesis had not been clarified in detail. Generally, it can still be said today that there is no peptic ulcer without proteolytic gastric acid. Differential-diagnostic measures usually succeed in differentiating the peptic formation of ulcers from psychogenic gastrointestinal malfunctions. The final diagnosis depends on X-ray results.

Bismuth Salts

Initially, treatment was based on administering antacids, such as magnesium or aluminum compounds, calcium carbonates, alkaline bismuth salts, e.g. bismuth aluminate, colloidal bismuth salts. A high relapse rate of over 80% and side effects, such as the rebound effect of acid secretion, deposits of aluminum and bismuth salts in the tissue to bismuth nephropathy, and bismuth encephalopathy forced the medical field to pursue new paths.

Surgery

The selective proximal vagotomy with surgical exclusion of the appropriate vagus branches or the acid-producing stomach sections in the case of relapsing stomach duodenal ulcers was another medical path that usually went nowhere. The relapse rate usually did not change with this serious surgical procedure.

$H_2$-Receptor Antagonists

In acid secretion, $H_2$-receptors are involved. The introduction of the $H_2$-receptor antagonists Cimetidine (Tagametg®) in 1977, and then Ranitidine (Zantic®, Sostril™) represented a milestone in medicinal ulcer therapy. This led to rapid pain elimination with the healing of UD and UV. Side effects of long-term therapy, such as infectious diarrhea, persistent hypergastrinemia with germ settlements on the antacid stomach lumen and nitrosamine formation, had to be accepted. Despite progress in acute therapy and the short-term prophylaxis of peptic lesions, the course of ulcers and the relapse rate has not been influenced by the $H_2$-receptor antagonists.

Inhibitors of the Proton Pump

The currently most potent molecule in the stemming of gastric acid is Omeprazol (Antrag®). It specifically blocks the $H^+/K^{30}$ adenosinetriphosphatases (ATP) of the mucosa of the stomach and thus hinders acid secretion. A suspected disadvantage is that, under permanent hypergastrinemia during Omeprazol therapy, a hyperplasia of neuroendocrine cells occurs and can lead to carcinoid tumors.

The high effectiveness compared to the $H_2$-receptor antagonists, however, led to shorter treatment times at lower dosage (20 mg/day). The relapse rate remained unchanged.

*Heliobacter Pylori* Infection

Marshall et al. only succeeded in 1983–1985 to prove the connection between the infection and gastritis through the rediscovery and ability to cultivate the germ *Campylobacter pylori* and through an oral infection in a self-test. This way the actual pathogenic factor of the ulcer was recognized. Initially, the germ was gained from biopsies of the antrum and corpus mucous membrane. In vitro cultivation did not succeed until later.

Bacteriology

According to examinations conducted by C. S. Goodwin, in Perth, Australia, the spiral-shaped *Campylobacter pylori* has little in common with other Campylobacter types (different fat composition, different enzyme metabolism, different genetic set-up). Therefore, it had to be renamed *Heliobacter pylori*.

Morphology

A spiral bent gram-negative germ, rods with lophotric flagellate, so-called clusters. Culturing is successful from stomach biopsies (antrum) on accumulation and selective media under microaerobic conditions of 90% $N_2$, 5% $CO_2$, 5% $O_2$ for 3–4 days.

Identification succeeds through additional proof of the enzymes oxidase, catalase, and urease. The germ is able to break down carbamide into ammonia in order to survive in an alkaline environment (cloud) in the acidic environment of the stomach.

Pathogenesis and Clinic

*H.p.* only occurs in humans and is transmitted fecal-orally. The pathogen infects and settles in the mucosa of the stomach.

*Heliobacter heilmanni*, a variation of *H.p.*, can be found in nearly all cats, dogs, and pigs. It can be passed on to humans. Infected people can develop disorders ranging from ulcers to stomach carcinomas.

Pathogenic Factors of *H.p.*

Due to the flagellated clusters, *H.p.* is particularly mobile and excels through increased adherence to surface cells of the stomach epithelium. The mucous membrane is attacked by proteases of the germn. Vacuolizing cytokinin (VacA), which destroys the epithelium cells, is released.

With the ELISA test, *H.p.* IgG antibody levels can be proven over an extended period of time, even after the infection has subsided. This immune reaction leads in turn to tissue damage. After the infection, an acute B-gastritis type develops. When untreated, the gastritis becomes chronic, and duodenal and stomach ulcers occur.

This can then develop into an adenocarcinoma of the stomach. The World Health Organization (WHO) has included *H.p.* into Category 4—Cancerogenes. The germ is to be interpreted as a resistance-weakening factor, which promotes early digestion of the mucosa of the stomach through the hydrochloric-acidic proteolytically active gastric Juice.

Therapy

Modern ulcer therapy has two goals:

1. alleviation of pain
   Initially, the patient is interested in quick relief of the pain and less in fast healing, i.e. *Heliobacter pylori* eradication.
2. prevent complications and relapse rate.

Reinfection

After an *H.p.* infection has healed, reinfection is to be avoided. Flies, e.g., can take on *H.p.* bacteria and excrete them in a form that is capable of living in their excreta. Foods must be covered, and general hygienic conditions must be improved as an important preventive measure.

Antibiotics Combination Therapy

After proof has been secured of *H.p.* following gastroscopy and removal of the mucosa of the stomach from the antrum or corpus, eradication of the germ through combination therapy is necessary. Serious *H.p.*-related forms of gastritis and underdevelopment should be treated in accordance with cancer prophylaxis—stomach carcinoma and lymphoma (MALT). Treatment turned out to be very difficult. Due to a high relapse rate, the mono- and dual-therapy was insufficient. For mono-therapy with bismuth compounds, and for dual-therapy with Amoxicillin and Omeprazol, the eradication rate was only between 35 and 60%.

Triple Therapy

Through the combination of bismuth, Amoxicillin and Metronidazol, healing was achieved for the first time in 85–95% of the cases after a 4-week treatment. The toxicity of this 3-fold combination, however, has not yet been clarified, especially when taking the long treatment time of 4 weeks into consideration.

Italian and French Triple Therapy

The triple therapy is a 7-day treatment with the proton pump inhibitor as well as two antibiotics.

Italian Triple Therapy: Clarithromycine and Metronidazol

French Triple Therapy: Clarithromycine and Amoxicillin

The medication must be taken twice daily each in standard dosages. This means that the patient must take 12 tablets a day. Also, there are side effects of the antibiotics, especially diarrhea, taste changes, etc. An antibiotics resistance development is also disadvantageous. *H.p.* resistance to Metronidazol and Amoxicillin has already been found.

There remains an urgent need in the art for improved methods of treating gastrointestinal ulcers or gastritis caused by microbial infections.

SUMMARY OF THE INVENTION

In accordance with the present invention, a method of treatment of infectious gastrointestinal ulcer disease or infectious gastritis disease of microbially infected gastrointestinal tissue in a mammal comprises administering to the mammal an antimicrobial amount of an antimicrobial medicament selected from the group consisting of antimicrobial medicaments which are cell wall constituent-inactivating by chemical reaction with cell wall constituents, endotoxin non-releasing, exotoxin-inactivating, and combinations thereof, so as to contact the infected gastrointestinal tissue with the antimicrobial medicament and treat the disease in the mammal. The invention also is applicable to compositions useful for treating infectious gastrointestinal ulcer disease and infectious gastritis disease.

DETAILED DESCRIPTION OF THE PREFERRED EMBODIMENTS

The antimicrobial compounds utilized in accordance with the invention are cell wall constituent-inactivating by chemical reaction with cell wall constituents, endotoxin non-releasing, and/or exotoxin inactivating antimicrobial compounds, which are slow-acting bactericides. Preferably, the compounds are cell wall-crosslinking compounds such as Taurolidine and Taurultam. Taurolidine is a unique antimicrobial agent having an exceptionally broad spectrum of antimicrobial and antibacterial activity including activity against gram positive and gram negative, aerobic, and anaerobic bacteria. Resistance has not been observed either in vivo or in vitro.

The compounds Taurolidine and Taurultam are as disclosed in U.S. Pat. No. 5,210,083, incorporated herein by reference.

The antimicrobial compounds utilized in the present invention are distinguished from conventional antibiotics as ordinarily understood in the art, i.e., antibiotics that act by attacking, breaking and/or rupturing microbial cell walls (disturbance of murein-biosynthesis, protein-biosynthesis, DNA topology, etc.), resulting in release of microbial toxins from the microbial cells.

While the invention is further described with respect to Taurolidine and Taurultam, the invention also is applicable to use of other cell wall constituent-inactivating, antimicrobial compounds which release no or substantially insignificant toxins. Thus, the invention is applicable to Taurolidine, Taurultam, and antimicrobial medicaments which act in a substantially similar manner.

Due to the complete bactericidal effectiveness of Taurolidine for the destruction of fine cell wall structures, Taurolidine is particularly suitable for the eradication of *H.p.* Adherence of the bacterium to the surface cells of the mucosa of the stomach is blocked so that the bacteria become a pathogenic. Additionally, bacteria cell walls become net-like so that the release of endotoxins (Zytotoxin VacA) is prevented.

With its microaerobic conditions, Taurolidine is especially effective towards anaerobics and *H.p.* The minimal inhibitory concentration (MIC) is about 70–128 mg/l, the minimal bactericidal concentration (MBC) is about 400–600 mg/l. Due to its chemical mechanism, the cell wall of the bacteria displays no resistance to Taurolidine, which is therefore particularly suitable for the antibacterial monotherapy of an *H.p.* infection.

Bactericidal Mono-Therapy with Taurolidine or Taurultam A slight temporary irritation or a burning of the stomach lining has become known as a side effect of Taurolidine or Taurultam. Through appropriate galenic formulation, such as the utilization of gel-forming agents which settle on the stomach mucosa and create a protective coating, the irritation can be suppressed almost completely.

Without being exhaustive, suitable antacids include: polysaccharides with antiphlogistic properties, protective colloids or polymers such as PVP, methylcellulose, carboxylmethylcellulose, methylhydroxypropylcellulose, gelatin, micro-crystalline collagen fibers, micro-crystalline cellulose, xanthan gum, tragacanth, dextrin, Macrogol 6000, glycogen, micro-crystalline rice starch, absorbent silicate, highly dispersed silicic acid, etc.

Micro-encapsulated compounds, which slowly release the active ingredient in the stomach without irritating the stomach lining, can also be produced. Dosages containing about 200–1,000 mg Taurolidine are possible, with about 300–500 mg Taurolidine being preferred. This makes it possible to get by with 1–2 tablets, coated tablets, dragees or capsules per day for 5 days to eradicate *H.p.* It is also possible to apply suspensions or syrup with a dosage of about 5 ml twice daily. 5 ml syrup contains 300 mg Taurolidine as the active ingredient.

Combination with Antacids

Another preferred combination is the application of Taurolidine together with an antacid in order to neutralize gastric acid and thus obtain faster pain alleviation.

The following compounds or combinations can be combined with the active ingredient Taurolidine:

natriumhydrogencarbonate, hydrotalcite, aluminum-magnesium-hydroxide-carbonate-hydrate, calcium carbonate, magnesium trisilicate, aluminum-magnesium-hydroxide-sulfate-hydrate (Magaldrate), aluminum-magnesium-silicate-hydrate, alkaline magnesium carbonate, calcium carbonate, etc.

The antacid is added to the tablet mixture or the granules to fill hard gelatin capsules. It can also be advantageous to add dry extracts out of licorice roots with a high content of glyceric acid, chamomile blossom dry extract, peppermint dry extract or other dry plant extracts such as yarrow milfoll, balm, salvia officinalis (sage), foeniculum vulgare (fennel) that are used for gastritis treatment, to the Taurolidine or Taurultam compound at a dosage of about 200 mg.

Preferred Forms

For increased efficacy of Taurolidine as well as prolongation of contact time on the mucosa of the stomach it is advantageous to use Taurolidine in micro-crystalline form. Preferred embodiments include formulations with high bioadhesion on mucous cells. The galenic form of preferred embodiments is an oral suspension with the addition of antacids such as Malgaldrate USP XXIII, with added stabilizers, and polymers with bioadhesive properties such as Carbopol™ resins of BF Goodrich.

In preferred embodiments, disintegration of the tablets in the stomach is swift, preferably into an amorphous to microcrystalline powder.

Substances with high mucous affinity and adhesion are the Carbopol™ types 934P and 971P. In addition to synthetic products, suitable additives include natural polymers and phytogums, such as gum arabic, xantan gum, pectin, agar, calcium alginate, etc.

Suitable tablet disintegrants with high mucuous tolerability include natural and semi-synthetic cellulose and starch products, such as microcrystalline cellulose, rice starch, carboxymethyl cellulose and hydroxyethyl cellulose.

The addition of milk powder or blood serum in some cases may be advantageous.

Combination with Proton Pump Inhibitor

A further preferred combination is Taurolidine in combination with a proton pump inhibitor (PPI) such as Omeprazol, Rabeprazol or the like. PPI's typically are prodrugs which are metabolized at a certain pH. Omeprazol metabolizes at a pH of about 3.9–4.1, whereas Rabeprazol metabolizes at a pH of about 4.9. Since Taurolidine is less irritating to the stomach at a pH of about 5, Rabeprazol is preferred when combined therewith. In particularly preferred embodiments, the sodium salt of Rabeprazol is utilized, with preferred dosages of Rabeprazol-Na of 10mg or 20 mg in the combination.

Without being exhaustive, a few examples are provided in order to explain the patent in greater detail.

EXAMPLES:

| Hard Gelatin Capsules |
| --- |
| CAPSUGEL, transparent, size 0 elongated |
| Contents: 300 mg Taurolidine (micro-crystalline) or Taurultam<br>6 mg Talc, Aerosil 200*, Mg-stearates 8:1:1 (additive)<br>100 mg Micro-crystalline rice starch |

| Hard Gelatin Capsules |
| --- |
| CAPSUGEL, transparent, size 0 |
| Contents: 300 mg Taurolidine or Taurultam<br>6 mg Talc, Aerosil 200*, Mg-stearates 8:1:1 (additive)<br>10 mg Omeprazol, micro-encapsulated, gastric juice-neutral |
| *Aerosil 200 = Colloidal Silicone |

| Tablets or Coated Tablets (direct tablet dispensing) |
| --- |
| Contents: 300 mg Taurolidine or Taurultam<br>200 mg Emdex ™*<br>10 mg Magnesium stearates<br>167 mg Ranitidine-HCl<br>5–10 mg Disintegrant for tablets** |
| Contents: 300 mg Taurolidine or Taurultam<br>500 mg Aluminum-magnesium-silicate-hydrate Aromatic substances and Saccharose<br>5–10 mg Disintegrant for tablets** |
| Contents: 250 mg Taurolidine or Taurultam<br>500 mg Calcium Carbonate<br>10 mg Magnesium stearates<br>60 mg Rice or corn starch<br>5–10 mg Disintegrant for tablets** |
| Contents: 200 mg Taurolidine<br>200 mg Emdex ™<br>10 mg Magnesuim stearates<br>10 mg Crospovidone USP 23/NF 18<br>200 mg fine dry powder of plants (33% yarrow milfoil herbal, 33% Camomilla flower, 33% Melissa foliate) |

| Taurolidine Tablets (Granule Production with subsequent dispensing) |
| --- |
| Contents: 350 mg Taurolidine<br>150 mg Aluminumhydroxide-magnesiumcarbonate complex<br>80 mg Corn starch<br>45 mg Kollidon 25<br>5 mg Aerosil 200*<br>40 mg Potato starch<br>15 mg Talcum siliconesatum 10%<br>15 mg Slip additives (Talc, Aerosil 200*, Mg-stearates 8:1:1 (additive) Aroma: strawberry, cocoa, saccharine<br>370 mg Alcohol 96% |

*Dextrates (Mendell Carmel, New York, U.S.A.)
**For example: Sodium carboxymethylstarch, Carboxymethylcellulose or Crospovidone
***Aerosil 200 = Colloidal Silicone Dioxide Production of the Granulates 1. Corn starch and Taurolidine are pre-mixed together with saccharine.
2. Kollidon 25 is dissolved in alcohol.
3. Aluminumhydroxyde-magnesiumcarbonate complex, pre-blended (see under 1.) as well as the remaining components, such as Aerosil 200, are mixed together in a blunger. The alcohol-damp mass is dried in a vacuum dryer at 30° C., and finally pressed through a 4 mm strainer, then a 2 mm strainer and thus refined into granules.

The dry granules obtained this way are finally mixed well with the potato starch, the slip additive, the talcum siliconesatum 10% and pressed into 700 mg tablets with a 13 mm stamp.

| Syrup | | |
|---|---|---|
| Contents: | 100 ml | Syrup contains: |
| | 6,000 mg | Taurolidine micr. or Taurultam |
| | 680 mg | Xanthan gum |
| | 680 mg | Carboxylmethylcellulose |
| | 20,000 mg | Saccharine Ph. Eur. 3 crystalline Vanilla, Aroma, Distilled Water 100 ml Per dose, 5 ml syrup (300 mg Taurolidine/ Taurultam) is taken twice daily. |

Taurolidine Tablets 200 mg
Aluminium Hydroxide Magnesium Carbonate FMA-11 H.D.
1. Composition:

| Substance | mg/Tabl. |
|---|---|
| Taurolidine | 200 |
| Emdex ™ | 90 |
| Starch 1500 | 90 |
| Aluminium Hydroxide Magnesium Carbonate FMA-11 H.D. | 50 |
| Talc | 16 |
| Mg-Stearate | 3 |
| Aerosil 200 | 1 |
| Tablet weight | 450 |

Taurolidine Tablets 300 mg
Aluminum Hydroxyde Magnesium Carbonate FMA-11 H.D.
1. Composition:

| Substance | mg/Tabl. |
|---|---|
| Taurolidine | 300 |
| Emdex ™ | 135 |
| Starch 1500 | 135 |
| Aluminum Hydroxyde Magnesium CarbonateFMA-11 H.D. | 75 |
| Talc | 24 |
| Mg-Stearate | 4.5 |
| Aerosil 200 | 1.5 |
| Tablet weight | 675 |

What is claimed is:

1. A method of treatment of infectious stomach disease caused by infection of gastrointestinal tissue with *Helicobacter pylori* in a mammal, comprising administering to said mammal an antimicrobial amount of an antimicrobial medicament selected from the group consisting of taurolidine, taurultam and a combination thereof, so as to contact said infected gastrointestinal tissue with said antimicrobial medicament and treat said disease in said mammal.

2. The method of claim 1 wherein said antimicrobial medicament is administered in a tablet, capsule, liquid, suspension or syrup.

3. The method of claim 1 wherein said antimicrobial medicament is administered at a dosage equivalent to about 200–1,000 mg taurolidine.

4. The method of claim 1 wherein said antimicrobial compound is administered at a dosage equivalent to about 300–500 mg taurolidine.

5. The method of claim 1 wherein said antimicrobial medicament is administered in combination with a pharmaceutically acceptable stomach-coating medication which forms a protective coating on a patient's stomach mucosa so as to prevent stomach irritation by said antimicrobial medicament.

6. The method of claim 1 wherein said antimicrobial medicament is administered in combination with a pharmaceutically acceptable gastric acid-neutralizing stomach antacid.

7. The method of claim 1 wherein said antimicrobial medicament is administered in combination with a proton pump inhibitor.

8. The method of claim 7 wherein said proton pump inhibitor is Omeprazol or Rabeprazol.

9. A pharmaceutical composition for treatment of an infectious stomach disease caused by infection of gastrointestinal tissue with *Helicobacter pylori* in a mammal, comprising an antimicrobial amount of an antimicrobial medicament selected from the group consisting of taurolidine, taurultam and a combination thereof, said pharmaceutical composition further comprising a pharmaceutically acceptable gastric acid-neutralizing stomach antacid.

10. A pharmaceutical composition for treatment of an infectious stomach disease caused by infection of gastrointestinal tissue with *Helicobacter pylori* in a mammal, comprising an antimicrobial amount of an antimicrobial medicament selected from the group consisting of Taurolidine, Taurultam and a combination thereof, said pharmaceutical composition further comprising a pharmaceutically acceptable proton pump inhibitor.

11. The pharmaceutical composition of claim 10 wherein said proton pump inhibitor is Omeprazol or Rabeprazol.

12. The pharmaceutical composition of claim 10 wherein said proton pump inhibitor is Rabeprazol.

13. The pharmaceutical composition of claim 9, further comprising a pharmaceutically acceptable, stomach-coating medication which forms a protective coating on a patient's stomach mucosa so as to prevent stomach irritation by said antimicrobial medicament.

* * * * *